(12) United States Patent
Jamieson

(10) Patent No.: US 7,492,949 B1
(45) Date of Patent: Feb. 17, 2009

(54) PROCESS AND SYSTEM FOR THE SEMANTIC SELECTION OF DOCUMENT TEMPLATES

(76) Inventor: Patrick William Jamieson, 10172 Parkshore Dr., Fishers, IN (US) 46038

( * ) Notice: Subject to any disclaimer, the term of this patent is extended or adjusted under 35 U.S.C. 154(b) by 675 days.

(21) Appl. No.: 11/231,225

(22) Filed: Sep. 20, 2005

(51) Int. Cl.
*G06K 9/68* (2006.01)
*G06K 9/64* (2006.01)
*G06F 17/27* (2006.01)

(52) U.S. Cl. .............................. 382/217; 382/305; 704/9
(58) Field of Classification Search ................. 382/181, 382/209, 217, 305; 358/403; 704/4, 9; 707/1–10
See application file for complete search history.

(56) References Cited

U.S. PATENT DOCUMENTS

| | | | |
|---|---|---|---|
| 4,914,590 A * | 4/1990 | Loatman et al. ................. | 704/8 |
| 5,267,155 A | 11/1993 | Buchanan et al. | |
| 5,523,945 A * | 6/1996 | Satoh et al. ..................... | 704/9 |
| 5,655,130 A | 8/1997 | Dodge et al. | |
| 5,684,999 A * | 11/1997 | Okamoto ........................ | 704/9 |
| 5,822,743 A | 10/1998 | Gupta et al. | |
| 5,899,989 A * | 5/1999 | Ikeuchi et al. .................. | 707/3 |
| 5,987,446 A * | 11/1999 | Corey et al. .................... | 707/3 |
| 6,182,095 B1 | 1/2001 | Leymaster et al. | |
| 6,263,335 B1 * | 7/2001 | Paik et al. ...................... | 707/5 |
| 7,302,383 B2 * | 11/2007 | Valles ............................ | 704/9 |
| 2003/0101056 A1 | 5/2003 | Howes | |
| 2004/0019855 A1 | 1/2004 | Purvis | |

OTHER PUBLICATIONS

Rebholz-Schuhmann D, Kirsch H, Couto F (2005) Facts from text—Is text mining ready to deliver? PLoS Biol 3(2): e65.

* cited by examiner

*Primary Examiner*—Daniel G Mariam

(57) ABSTRACT

Document templates could improve the speed, cost, and quality of documentation if appropriate templates could be located without undue selection burden. Semantic retrieval (IR) can greatly improve the precision of finding relevant document templates. The present invention discloses a process which implements a semantic information retrieval system to locate template documents, using as search vectors the semantic content of sentences from a new partially completed document. The system enables the author to quickly and easily transfer sentences from template documents into the new document. The system provides options for the author to match against specialized template collections and subsets of template documents. A significant advantage of the present invention over other template based methods is ability to retrieve a relevant template document when there are many thousands of exemplar documents without having to construct a formal query.

15 Claims, 6 Drawing Sheets

Fig. 4

PROCESS AND SYSTEM FOR THE SEMANTIC SELECTION OF DOCUMENT TEMPLATES

FEDERALLY SPONSORED RESEARCH

The invention described herein was funded in part by a grant from the National Library of Medicine, Grant # 1 R43LM008974-01. The United States Government may have certain rights to the invention.

CROSS REFERENCE TO RELATED APPLICATIONS

The following co-pending U.S. patent applications are hereby fully incorporated by reference, "Process for constructing a semantic knowledge base using a document corpus", Ser. No. 10/844,912, filed on May 13, 2004, and "Process and System for High Precision Semantic Document Retrieval", Ser. No. 11/156,841, filed on Jun. 20, 2005.

SEQUENCE LISTING OR PROGRAM

None.

FIELD

The present invention relates to a method and system for producing documents from document templates and, more specifically using semantic analysis to select the most relevant templates.

BACKGROUND

There is tremendous inefficiency in the preparation of reports, frequently containing similar content, but requiring costly dictation and transcription. In the medical field, many reports contain repetitive information, especially normal reports. Radiology, pathology, and surgery reports often include similar information depending on the context of the test, biopsy, or surgery being performed. Because of the high cost of producing medical reports, estimated at 6-7 billion dollars/year in the United States, individuals and companies are actively seeking to lower costs and improve efficiency using computerized document solutions.

One semi-automated documentation technique which has lowered reporting cost uses templates. Templates are outlines that structure text into blocks, paragraphs, or sentences. Typically, they contain delimiters designed to serve as placeholders for variable text regions that are later completed (instantiated) to produce a document. Templates organize documents and provide "canned" text for phrases, sentences, or document elements that are used repetitively. Templates can improve data collection by reducing missing, incorrect, and inconsistent data. Template elements, e.g. sentences, also can be uniquely identified and stored within a relational database. If more professionals created documents with templates, documents could also be processed more readily in data mining, decision support, and text summarization applications.

Some templates are professionally authored with the specific goal of serving as a base document for newly created documents. Other templates may consist simply of old documents, repurposed to serve as templates. For example, retrieving an old document to a business partner, and saving it as a new document after making minor changes. Either type of template may be useful. The key is locating a closely related "neighbor" document.

Howes (USTPO application 20030101056) described a computerized system for completing normal medical reports. The author first selects a master template from a template repository, and then completes the template with unique case information. However, this approach breaks down when there are many document types. For example, a radiology report for a normal head computed tomography scan, is vastly different from a report documenting left cerebral hemorrhage. In these complex cases, it may be impossible to create a report in the same manner as one fills out a form, using simple fill in the blanks or check boxes. Although a physician might wish to select sentences rather than write them from scratch, the information conveyed is sensitive to the problem-context (also called the document type or document context). Unfortunately, in medicine as well as other complex domains, authors communicate a great deal of non-stereotyped knowledge, difficult to encode in a few master templates. The greater the range of a professional's domain knowledge, the more difficult it is to build a complete master template repository.

Automated document systems employing template elements, consisting of phrases or sentences, have been used to speed document generation in simple or narrow problem-contexts. Dodge et. al. (U.S. Pat. No. 5,655,130) described a method for producing a variety of documents from a common document database partitioned into a number of encapsulated data elements. As in other template systems, creation and selection of these elements was a manual process. Leymaster et al. (U.S. Pat. No. 6,182,095) developed an interactive computer system to display document structures used in report generation. Selecting the correct template involved explicit user questioning. Other document generation systems use a variety of computer interfaces such as trees, nested menus, and check boxes. When the user selects an item, it is added to the document. Buchanan (U.S. Pat. No. 5,267,155) employed such a method to generate patient reports. Like other template management systems, the user must first develop a master template database from scratch, and then remember the association between the template's name and its contents. While this may not be such a serious problem when only a few templates are needed to cover a domain, when potentially hundreds or thousands of templates are needed for describing complex information, template building and selection becomes intractable. Current template systems suffer undesirable tradeoffs—creating more templates increases the probability that a template can be found which is close to the new document the author wishes to produce, while at the same time increasing the cost and effort of building templates, and the burden of selecting them.

Case Based Reasoning (CBR) provides a related but potentially more advanced mechanism for building a document and template management system. CBR can recall relevant reports, which can then serve as templates, based on previous reports (cases) stored in memory. The CBR user would: (1) retrieve relevant reports (2) reuse some of the report information in the current report (3) revise the report, and (4) retain the new report in the system. The essential step is finding one or more prior reports that are similar to the current report. It is unlikely that any one report will be a perfect match to the case being reported; only some of the information is likely to be used. A documentation system which could find the relevant "neighbor" reports to serve as templates could speed the creation of new reports.

Purvis (USTPO application 20040019855) disclosed a CBR system, which used previously created documents stored in a case base, and methods for drawing upon these documents to create a new document. However, her system was mainly targeted to helping authors select the correct formatting and layout of a report, and was not a true text case-based reasoning (TCBR) system, which is necessary for finding similar report content.

Gupta et. al. (U.S. Pat. No. 5,822,743) disclosed a CBR system for solving problems within a selected knowledge domain. Users retrieved solved cases using one or more case attributes. Matching algorithms generated a list of potential solutions. This system did not attempt to extract the meaning from free text reports, and was not used to facilitate document creation.

Finding relevant template documents rapidly is a major unsolved problem TCBR systems must overcome to effectively assist users in document creation. Two dimensions are often measured to judge the quality of case retrieval. Recall measures the completeness of retrieving documents or cases. Precision measures the specificity of returning only relevant cases. Users want the templates to provide similar content desired by the author. Unfortunately, current TCBR systems based on conventional information retrieval technology have relatively poor recall and precision.

TCBR systems using metadata or keyword attributes have significant indexing problems because the semantics of language is complex. Indexing documents by keywords often results in poor precision, because the meaning of document sentences is not just a product of the individual words, but their roles (nouns, verbs, clauses, modifiers, etc.) and interrelationships. Additionally, semantic information may be implicit—depending on the document context or the knowledge domain, making it very difficult to semantically index a document without a great deal of labor.

The development of high precision TCBR system requires a deep understanding of a knowledge domain. To be effective in locating relevant reports which may serve as templates, it must know how to identify linguistic expressions that are semantically equivalent. However, computational linguists have not yet developed tools which can analyze more than 30% of English sentences and transform them into structured forms [Rebholz-Schuhmann D, Kirsch H, Couto F (2005) Facts from text—Is text mining ready to deliver? PLoS Biol 3(2): e65]. Without identifying most of the linguistic variations that represent the same concept semantically in the case base, the TCBR system will have low precision and recall, and thus limited utility in template selection.

Another type of CBR system uses an expert system, a knowledge base, and a question/answer list designed in such a way that the expert system can usually return the correct case. Building the question/answer section is manpower intensive and may require 70-80% of the total development time. A domain, such as radiology, has thousands of individual concepts. Creating templates and questions for all these concepts would be a significant challenge because no tools exist to automatically extract them. Even after the template database is initially created, there would be an ongoing need for incorporating new ideas, changes in medical terminology, and new procedures. Any CBR system proposed for document generation must deal with these issues.

A CBR system designed for medical reporting must work within the constraint of limited selection time. As the time the CBR system needs to find the correct template increases, its value for producing a new document using this method decreases. At some point, when the burden of selection becomes too high, the author will find it more advantageous to create the material from scratch. Multiple question CBR systems extract a significant time burden. Rapid, high precision TCBR systems for selecting document templates do not exist.

Another problem with a traditional CBR system is that users may be unwilling to interrupt their workflow to retrieve template documents. If sentences from a partially completed documented could be used to retrieve templates without any user intervention, the computer-assisted system would have greater acceptance. Such a system does not exist.

After the reports are retrieved, sentences from the reports must be transferred to the new report under construction. Since the user is likely to have very specific ideas about which sentences add the greatest value to her report, a method for selecting and transferring these sentences is needed that is considerably quicker than electronic cut and paste. No exemplar CBR systems, which retrieve multiple document templates, propose methods to speed information transfer into new documents.

In summary, a semi-automated document system selecting old reports to serve as templates, or professionally authored templates, would be particularly advantageous for physicians, attorneys, or other individuals who prepare reports, if there were good methods to find a reasonably small but specific list of similar reports, and this content was easily accessible without undue burdens on the user's memory or time. The present invention accomplishes this through a high precision TCBR system. The invention facilitates template selection because it has a semantic understanding of the knowledge domain. Relevant templates are returned in near real-time from limited information available in partially completed reports. The invention employs a visual interface which permits information contained in template document (s) to be rapidly and selectively transferred into a new document. Prior art systems are unable to meet these demanding requirements.

OBJECTS AND ADVANTAGES

Thus, an object of this invention is to overcome these and other inadequacies of existing template documentation systems. A primary object of the present invention is to provide a novel method and system for retrieving similar documents to serve as document templates, using high precision semantic indexing, in order to facilitate the completion of a new document.

Another object of this invention is a method to rapidly display template documents after the author has written or spoken a few sentences in the new document, so as not to burden the user with creating a formal query to find a template document.

A related object of this invention is an intuitive display which enables an author to retrieve template documents based on the concepts of greatest importance to the author.

Yet another object of this invention is a method for transferring portions of the template document easily into a new document.

Another object of this invention is a method which enables authors to retrieve document templates from a personal repository, department or company collection, or general document store, depending on author preference.

Still another object of the present invention is a method to display only particular sentences from template document, such as treatment recommendations, depending on author preference.

SUMMARY OF THE INVENTION

The present invention builds upon "Process and System for High Precision Semantic Document Retrieval", Ser. No. 11/156,841, which facilitates the selection of documents through semantic retrieval. That invention disclosed a process for retrieving documents through a semantic query consisting of one or more propositions, or declarative statements. In accordance with one illustrative embodiment, the present invention takes sentences from a new document, and maps them to one or more semantic proposition(s). These propositions are then used as search vectors into the template document collection. The system returns the most specific template documents which contain all the search vectors (a Boolean "AND" operation). However, another aspect of the invention, allows the author to relax this constraint by indicating only those search vectors of interest. After the system retrieves the template documents, it facilitates the rapid transfer of specific sentences into a new document. In accordance with another aspect of the present invention, the template retrieval system can match against specific template document collections which may include the author's personal collection, a departmental or company wide template library, or a larger repository of enterprise wide template documents. By segmenting template documents into sections, the present invention can also match against sections of the template documents. Although the examples are taken from the radiology domain, the process and system are general and can be used in any knowledge domain that can be reasonably circumscribed by a large document collection.

DRAWINGS

These and other features of the Subject Invention will be better understood in relation to the Detailed Description taken in conjunction with the drawings, of which:

FIG. 1 is a bitmap rendering of three computer screens displaying one embodiment of a computer interface showing a sentence acquired while creating a new document, semantic decomposition of this sentence, and display of one document template.

FIG. 2 is a bitmap rendering of a computer screen showing one embodiment of a computer interface displaying the result of finding 400 document templates, the decomposition into a plurality of sentences of one said template, and the selection of one said sentence for inclusion into a new document.

FIG. 3 is a bitmap rendering of a computer screen displaying one embodiment of a computer interface showing the result of selecting the sentences from the document template: "No focal opacities are present within the lungs", and "Chest xray within normal limits" and their inclusion into a new document.

Figure 4:
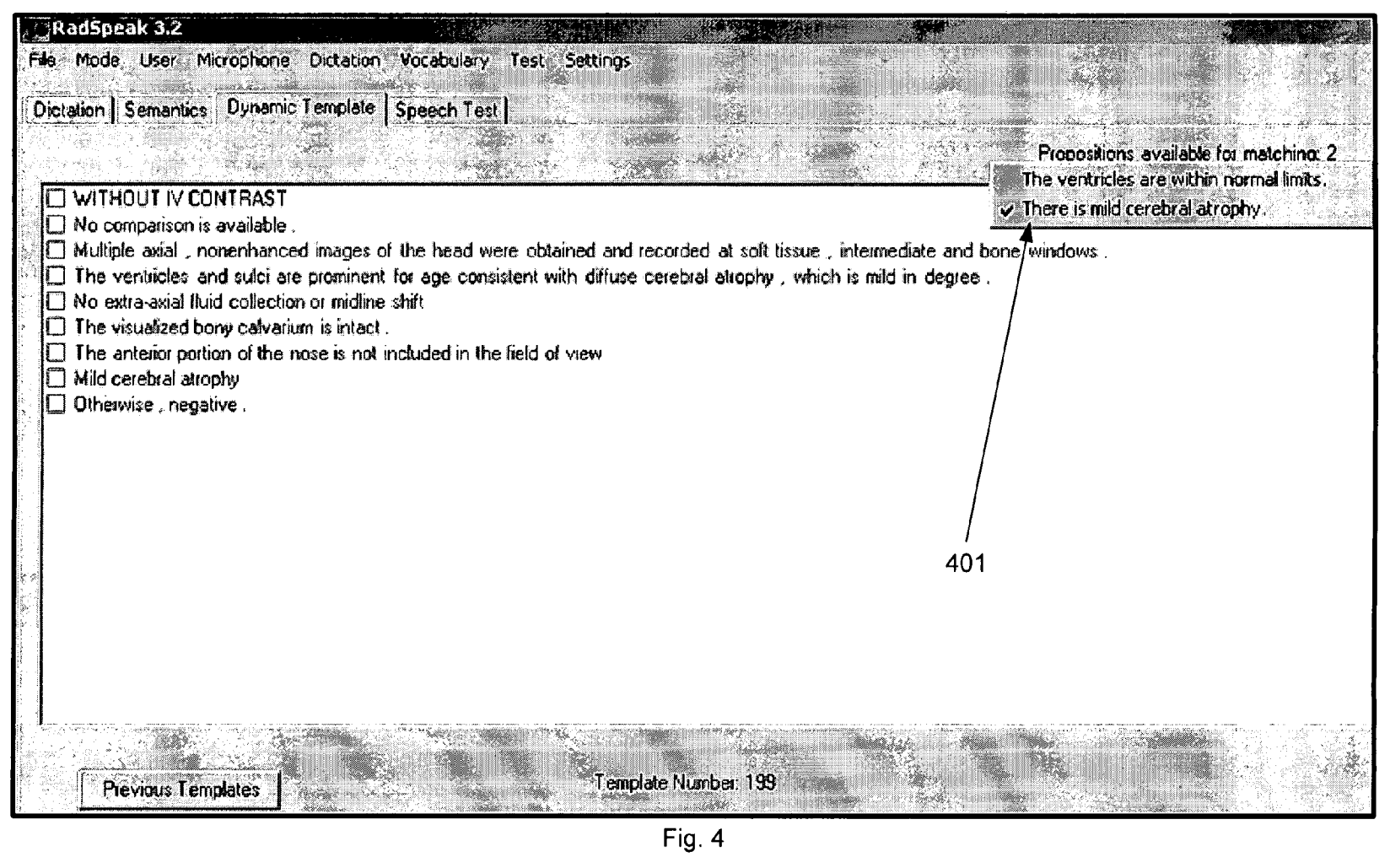

FIG. 4 is a bitmap rendering of a computer screen showing the selection of just one proposition to serve as the "search vector" for locating document templates.

FIG. 5 depicts a high-level block diagram of the semantic template retrieval system in accordance with the present invention.

FIG. 6 is a flowchart of the inventive retrieval process using the components shown in FIG. 5, illustrating the steps the semantic template system employs to find template documents.

Understanding that these drawings depict only typical embodiments of the invention and are not to be construed to limit its scope, the invention will be described in detail below.

DETAILED DESCRIPTION OF THE PREFERRED EMBODIMENTS

While the present invention is contemplated for use in a wide variety of knowledge domains, it is described herein, primarily in the context of a documentation system for radiology for the purpose of illustration only.

The present invention employs several knowledge base components described in application Ser. No. 10/844,912 titled, "Process for constructing a semantic knowledge base using a document corpus, herein referred to as "corpus based knowledge construction". Briefly, that invention describes the steps for mapping the set S of sentences in a corpus of related documents, to the set M, of unique meanings or propositions in a knowledge domain to form a semantic knowledge base. A knowledge domain is the semantic knowledge contained in a large corpus of related documents from the domain, for example the semantic knowledge in 500,000 radiology reports. The fundamental unit asserted in the semantic knowledge base is a proposition expressed as a declarative sentence, conveying the underlying meaning of a document sentence. Propositions are distinct from the sentences that convey them, although they are related. For example, the sentences "The chest x-ray is normal" and "The chest x-ray is within normal limits" map to the same proposition or meaning. The knowledge-base designer creates propositions in a semi-automated fashion by drawing from common sentences in the corpus using software tools. By mapping sentence variants to the same proposition, the equivalence of different free-text sentences is accurate because strong methods of string matching are used, over weaker statistical methods. Propositions and sentence mappings are systematically created to fully characterize the semantic knowledge of a domain. The current invention uses the semantic knowledge base, and a table that associates free-text sentences with their underlying propositions from this earlier work.

The present invention also uses a query component disclosed in "Process and System for High Precision Semantic Document Retrieval", Ser. No. 11/156,841, herein referred to as semantic document retrieval. The query component in that invention matches semantic proposition(s), which represent the knowledge contained in the query, to semantic propositions indexed in a document collection. The semantic query system returns documents closely matching the query with very high precision.

The following definitions may be useful.

DEFINITION LIST 1

Term: Proposition
Definition: Atomic unit of semantic meaning capturing in whole or part the knowledge within a declarative sentence.

Term: Knowledge domain
Definition: The set of all propositions that represent the knowledge within a specialized field of study such as radiology as derived from a document corpus.

Term: Corpus
Definition: A large collection of related documents or reports from which a semantic knowledge base can be derived, and from which similar documents to a new document can be found.

Term: Mapping Table
Definition: A table, usually in the form of a relational database table, which holds the relations between unique sentences in the corpus and semantic proposition (s).

Term: Case Based Reasoning
Definition: A process where similar cases are retrieved to the case being solved. In the case of a documentation system, finding a similar document template to a new partially completed document.

Term: Template
Definition: A document that provides content to complete another document. A template that is semantically close to a new document is a "relevant" template.

Term: Template Sentence
Definition: A sentence from a template document that can be transferred into a new document.

Term: Search Vector
Definition: A proposition extracted from a new document, which serves in a semantic query into the template document collection.

Term: Partial Solution Set
Definition: A collection of template documents returned by the present invention which contains the result of matching one semantic proposition in the query to the same proposition in the new document.

Term: Solution Set
Definition: A collection of template documents returned by the present invention that satisfies all the Boolean criteria of the semantic query.

EXPLANATION OF FIGURES

With this in mind.

With reference to FIG. 4, an additional example of the template interface is shown where the user has right "clicked" on component (401) to reveal the propositions extracted from the sentences in the documentation interface. The user in this example has selected only the proposition, "There is mild cerebral atrophy". In this case template documents are returned from the partial solution set for this proposition. The system normally defaults to finding the solution set through a Boolean "AND" operation on all the partial solution sets corresponding to each proposition as described in semantic document retrieval. The user can also select more than a single proposition. In that case a Boolean "AND" operation on the partial solution sets for these propositions is performed.

The document collection contains not only completed documents, but documents authored specifically for use as templates (505). These exemplar documents may contain information a specific author thinks is especially important—a personal template collection. Additionally, a department or company may maintain a collection of template documents that professionals judge to be useful in particular contexts. By organizing templates into collections, the CBR system can retrieve only those templates based on author preference or department or company policy. The process the CBR uses to match these narrower document collections is exactly the same process for all template documents, as shown in FIG. 6.

Figure 1:
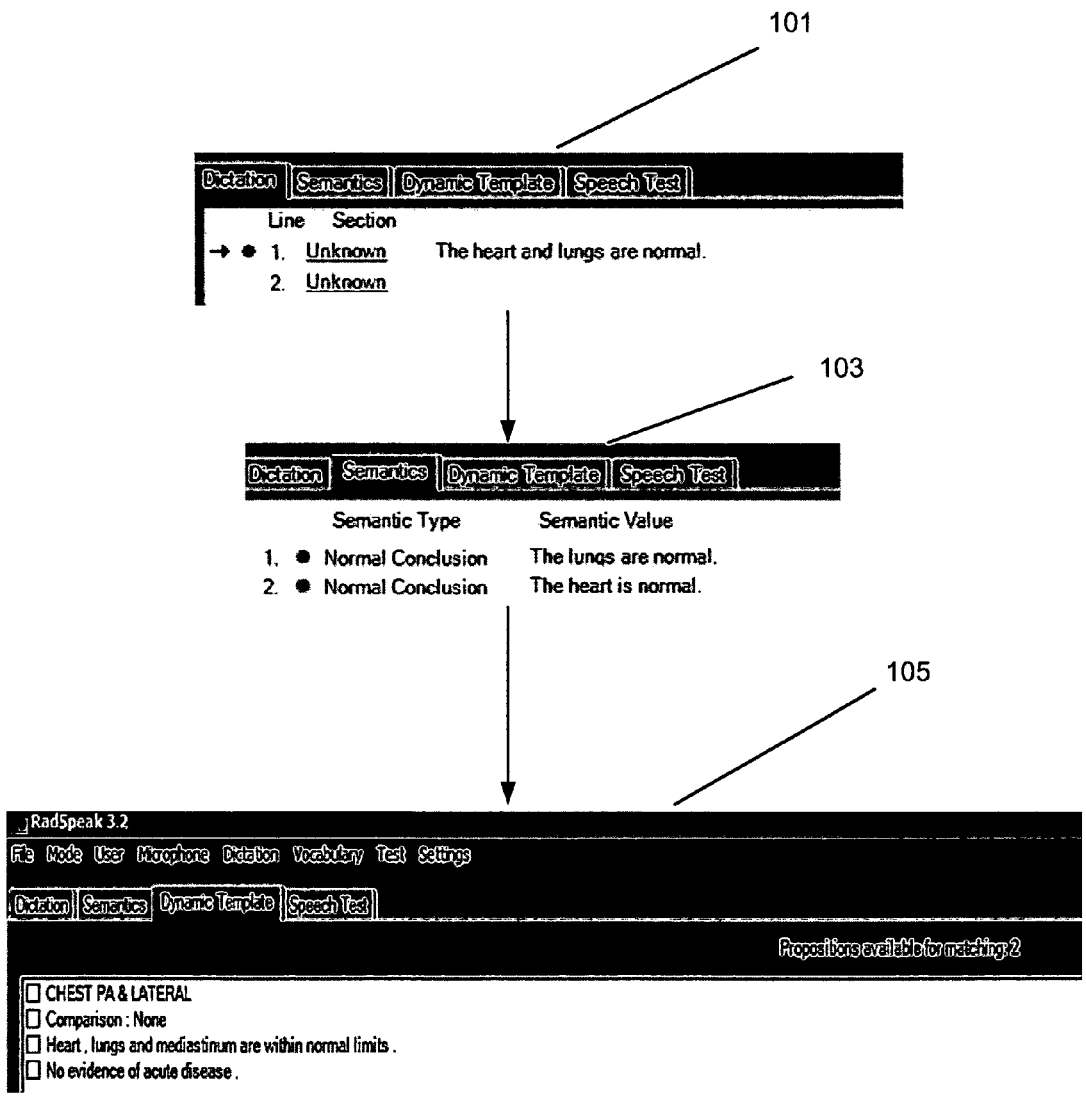
FIG. 1 depicts one embodiment of three visual interfaces depicting the workflow of the present invention. The documentation interface (101) displays the result of the user dictating using speech recognition the sentence "The heart and lungs are normal." The user could have also typed the sentence with a word processor. The dot next to the sentence indicates the system recognizes the sentence, since it matches a sentence in its database of known domain sentences, as described in corpus based knowledge construction. The semantic interface (103) shows the corresponding semantic proposition(s) to this sentence. The semantic proposition(s) are retrieved by looking them up in the mapping table of the semantic knowledge base as described in corpus based knowledge construction. These propositions serve as semantic "search vectors" into the template document collection. The query component matches these semantic proposition(s), which represent the knowledge contained in the partially completed document, to semantic propositions indexed over the entire template document collection as described in semantic document retrieval. Each proposition returns a distinct collection of document templates called the partial solution set. The template interface (105) shows the first template returned after applying a Boolean "AND" operation to all the partial solution sets, called the solution set. Each template is displayed as individual sentences to facilitate selection into a new document.
Figure 2:
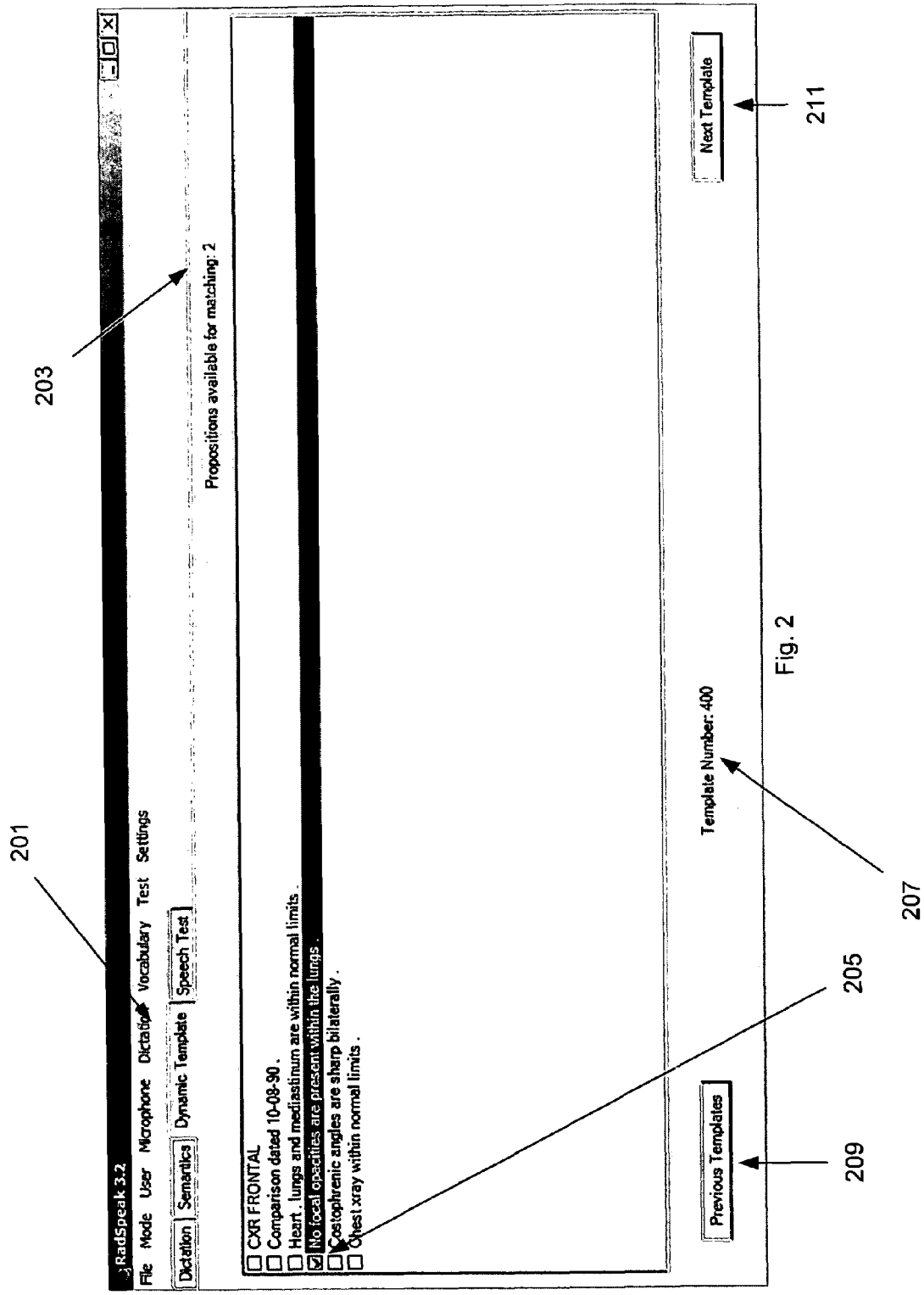
FIG. 2 shows a close up view of the visual interface of the preferred embodiment of the template interface. Component (201) depicts a tab on a visual control which allows the user to quickly navigate between the documentation interface and the template interface. This is advantageous for remembering what sentences are already in the new partially completed document. Component (203) shows the number of propositions extracted from the new partially completed document. The user can right "click" with a mouse (not shown) to reveal the individual propositions, which were extracted. The user can select one or more template sentences (205) by "checking" the check box next to the sentence. Each selected sentence is added to the new document. A label (207) identifies the number of document templates available, which are close semantically to the new document. Buttons (209, 211) allow the user to retrieve the previous or next template respectively.
Figure 3:
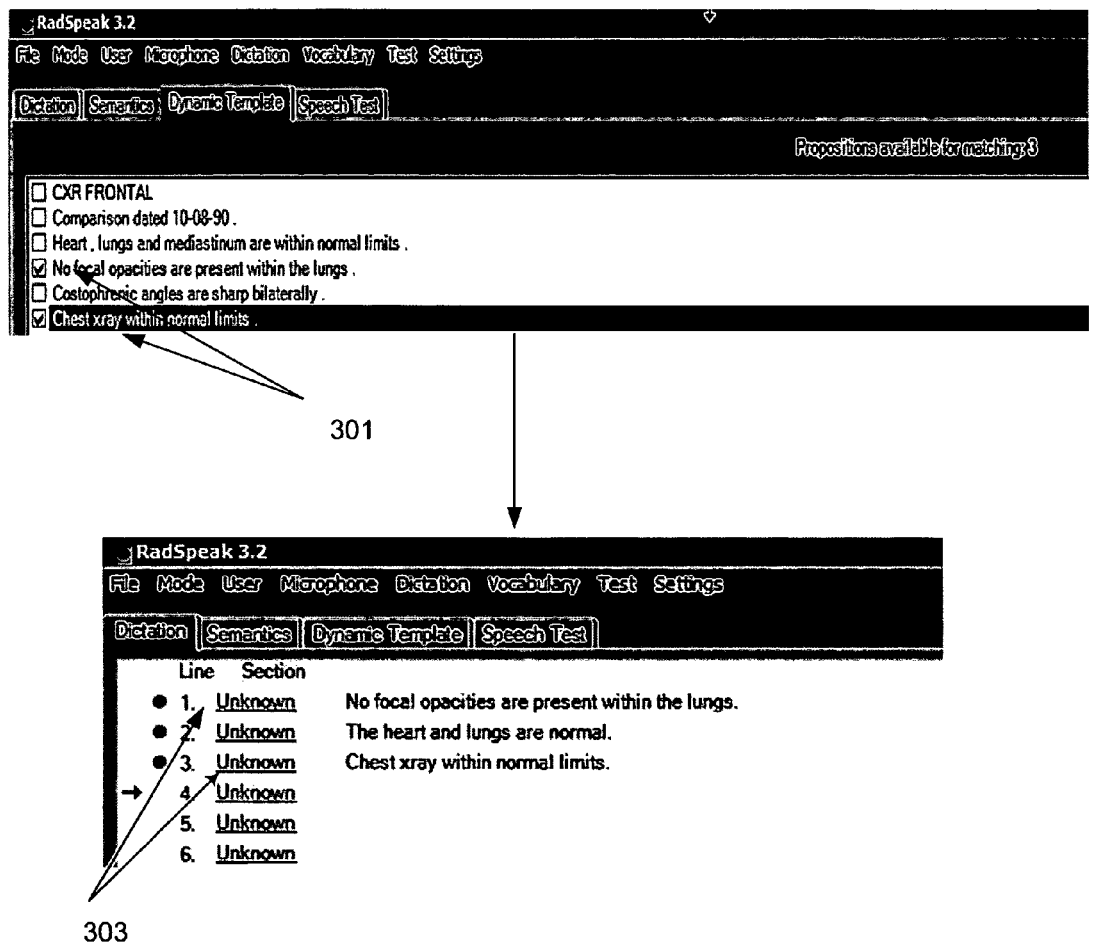
FIG. 3 shows an example of a user adding the sentences "No focal opacities are present within the lungs" and "Chest xray within normal limits". The user "checks" these sentences through checkboxes (301) in the template interface, and the sentences are then transferred to the partially completed document shown in the documentation interface (303). The user can quickly navigate through many template documents, selecting useful sentences, and transferring them to the new document.
Figure 5:
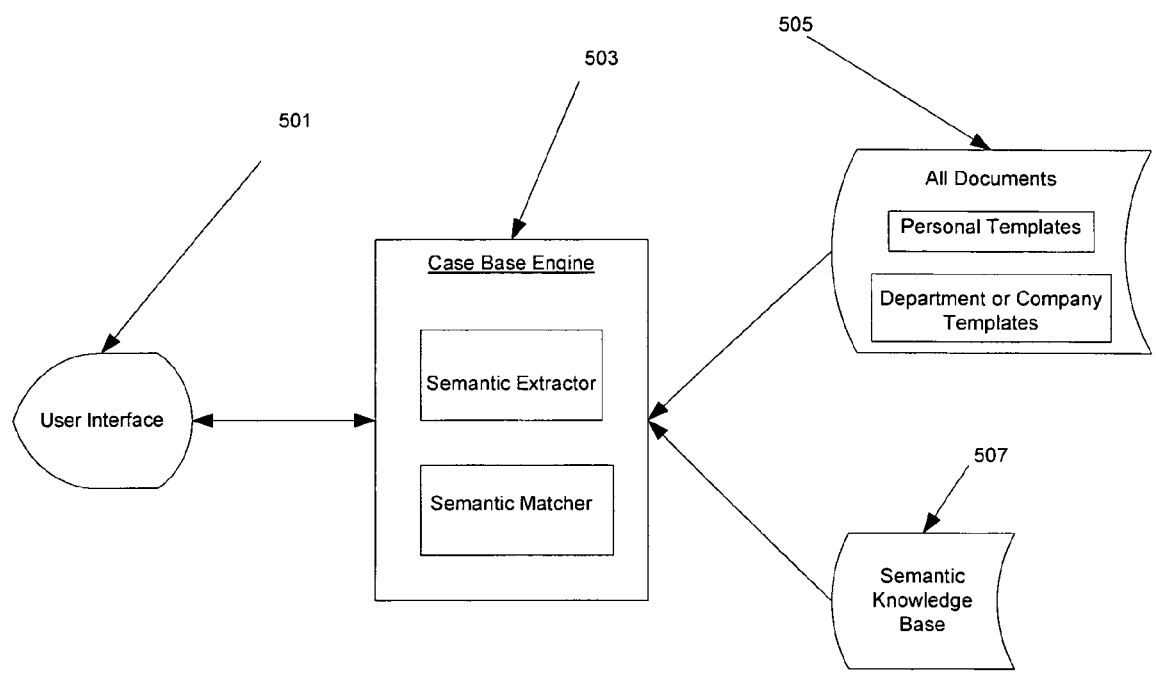
FIG. 5 depicts a high level block diagram of the components of the semantic template retrieval system. The user interface (501) consists of multiple views shown in FIG. 1, including the documentation interface (101), semantic interface (103), and the template interface (105). The interfaces communicate with the Case Base Engine (505), or CBR. Sentences are acquired through the documentation interface. A semantic extractor then looks up the meaning of the sentence in the mapping table as described in corpus based knowledge construction. The mapping table maintains a correspondence between sentences and semantic proposition(s). The extracted propositions are displayed in the semantic interface. The semantic matcher is the key component of the Case Base Engine (505) because it retrieves close document templates as described in semantic document retrieval. This component is shown in FIG. 6, and will be explained more fully shortly. A database of template documents (505) includes personal templates, departmental or company wide templates, or enterprise wide template documents available to the CBR. Each of these documents is first semantically indexed at the sentence level for use by the CBR as described in detail in corpus based knowledge construction. Briefly a document collection (505), or corpus, defines the knowledge domain and provides all the documents to be semantically indexed. The document collection is first segmented into unique sentences. Unique propositions are then created, which codify the meaning of these sentences, using the process and methods taught in corpus based knowledge construction and added to a Semantic Knowledge Base (507). A knowledge engineer using semi-automated methods performs semantic annotation of the sentences, linking one or more propositions to them to construct a mapping table. The mapping table is able to associate the linguistic expression of any sentence with its underlying semantic meaning. The document collection is also indexed by each sentence in the document.
Figure 6:
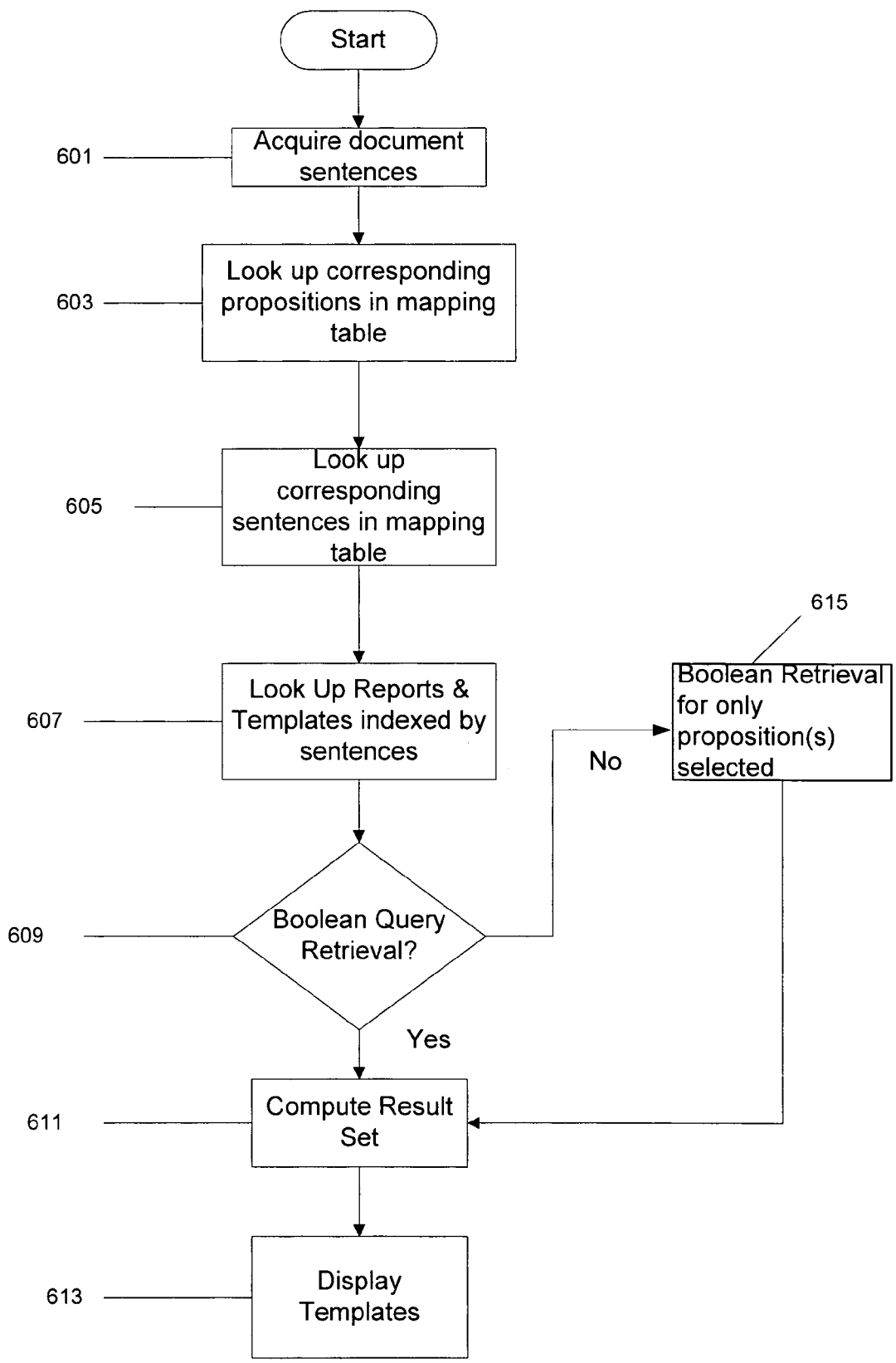

FIG. 6 shows a flowchart describing the steps for semantic based template retrieval. The first step (601) requires the user to input one or more sentences using either a word processor or speech recognition. If the user does not mark the end of each sentence, those knowledgeable in the art of natural language processing can use text segmentation techniques to determine the sentence boundary. Next the CBR engine (503) extracts the meaning of these sentences (603) by looking up the corresponding proposition in the mapping table (507) described in corpus based knowledge construction. The mapping table is a relational database table that contains a row for each sentence and its corresponding proposition(s) in the semantic knowledge base. Each sentence may have one or more propositions. The CBR engine (503) then looks up all the sentences associated with these propositions (605) using the mapping table (507) as described in semantic document retrieval. This step is necessary to order to find all the different sentence expressions which are equivalent in meaning to the proposition under consideration. In step (607), all the reports are searched which contain the sentences located in step (605). The result of the CBR engine's (503) semantic matching operation is a set of template documents similar in content to the new partially completed document. For each proposition, the set of template documents, called the partial solution set is located. In some circumstances, the user may be only interested in retrieving documents containing one proposition. In this case, the partial solution set is the solution set.

The user can also restrict the matching operation to subsets of documents or templates such as a personal collection of template documents or a company wide template collection. The same method can be used to restrict matching to sentences contained in particular sections of the template document. For example, matching only sentences within the "recommendation" section. Every document in the repository (505) is assigned a unique identifier. Each sentence and its corresponding section attribute are stored in a table linked to the template document by its unique identifier. Those knowledgeable in relational database design will appreciate different techniques for laying out the storage of the documents, sentences, and sections that allow for template retrieval given a sentence as a key.

In the preferred embodiment, the default step is to perform a Boolean "AND" operation (609) on all the partial solution sets. This provides the most specific template documents which match the semantic content in the new document up to that point. Those knowledgeable in computer algorithms know many efficient ways for computing Boolean "AND" operations over sets. The resulting solution set is returned in step (611) and displayed in the template interface in step (613). If the user does not want this default behavior, a different set of propositions can be selected (615) and a Boolean "AND" operation applied to only this set of propositions. The user can rapidly display each template in the partial or total solution set by "clicking" the "next" or "previous" button on the template interface. The interface tracks the current position within the solution set and advances or decrements the position depending on whether the user clicks "next" or "previous" respectively. The template interface also displays the total number of templates (207), and the number of propositions extracted from the partially completed document (203).

The method of the present invention can be realized in a centralized fashion in one computer system or in a distributed fashion where different elements are spread across interconnected computer systems over a network. A typical combination of hardware and software consist of a general purpose server computer system employing a relational database engine for storing and retrieving documents, sentences, propositions, and the mapping table. A separate client computer using a microprocessor and software program could display the visual interface for a query application and produce the screen displays shown in FIGS. 1, 2, 3, and 4. The client machine communicates to the database engine over a computer network, which may consist of either an intranet or wide area network such as the internet. In the preferred embodiment the programming platform includes C#.NET™ and ADO.NET™ for building the client query application, and SQL-Server™ for building the relational database engine and server application. However, nothing about the described invention requires this combination of computing resources or languages. Any relational database engine that can be queried from client computer could be used to construct the semantic retrieval application. The client or server software could be constructed to include program modules consisting of objects, components, data structures, stored procedures, etc. that implement particular tasks of the overall program. Moreover, those skilled in the art will appreciate that the invention may be practiced with other computer system configurations, including hand-held devices, multiprocessor systems, microprocessor-based or programmable consumer electronics, network PCs, minicomputers, mainframe computers, and the like. For a distributed computing environment, program modules may be located in both local and remote memory storage devices. Those versed in the art of computer programming will appreciate the wide range of platforms and software elements which could be used to create particular embodiments of the invention.

DESCRIPTION AND OPERATION OF ALTERNATIVE EMBODIMENTS

Documentation systems increasing employ a wide range of hardware configurations including tablet personal computers, handhelds, mobile phones, and other devices. The present invention could be implemented on all these devices restricted only by their memory and storage limitations.

Speech recognition is a relatively new but very important tool in documentation. The present invention makes also can make use of a commercial speech recognizer, ViaVoice™ version 10.0 by International Business Machines, to acquire sentences in step (601). However, in the preferred embodiment the user just types a sentence into a text box or word processor to input a sentence.

ADVANTAGES

From the description above, a number of advantages of my method for semantically retrieving document templates become evident:

The template retrieval system has very high precision because only templates which match the content of sentences in a new partially completed document are retrieved. This high precision makes it likely that some of the other sentences in these related or "neighbor" template documents can be used to complete the new document.

The user does not have to formulate a query to find relevant documents as in other CBR systems, which for many users has an unacceptable time cost.

The user does not have to remember the name of a particular template, which can be very difficult when there are hundreds or thousands of templates.

The user can rapidly retrieve template documents that match a portion of the content of greatest interest to the author.

The user can quickly scan, select, and transfer sentences from template documents into the new document under construction.

The user can match subsets of template documents from either a personal collection or departmental or company wide repository of template documents.

The database of template documents can be easily extended as new documents are added, in contrast to other template systems which would require additional engineering.

Although the description above contains many specifics, these should not be construed as limiting the scope of the invention but merely providing illustrations of some of the presently preferred embodiments. Thus the scope of the invention should be determined by the appended claims and their legal equivalents, rather than by the examples given.

What is claimed is:

1. A process for semantically selecting a document template, comprising:
    (a) acquiring an input sentence, and
    (b) a processor for performing the following steps: looking up corresponding sentential proposition(s) to said sentence in a mapping table created by domain experts and,
    (c) looking up corresponding sentence(s) to said sentential proposition(s) in said mapping table and,
    (c) retrieving document templates from a template document collection that contain one or more of said sentences,
Whereby a partial solution set of document templates for each said sentential proposition is returned.

2. The method according to claim 1 where the input sentence is acquired through speech recognition.

3. The method according to claim 1 where the input sentence is acquired through a word processor.

4. The method according to claim 1 where all the sentences in a document under construction are processed and a list of corresponding proposition(s) are displayed.

5. The method according claim 1 wherein sentence(s) from a template document in the partial solution set are displayed as a list which are transferred to a new document under construction in response to user selection.

6. The method according to claim 1 wherein a count of unique documents in the partial solution set for each proposition is displayed.

7. The method according to claim 1 wherein a user restricts the documents from the partial solution set to a subset consisting of either personal templates, departmental templates, or company wide templates, or any combination thereof.

8. The method according to claim 1 wherein a user restricts the sentences for look up to specific sections within the template document collection.

9. A process for semantically selecting a document template, comprising:
    (a) acquiring input sentence(s), and
    (b) a processor for performing the following steps: looking up corresponding sentential proposition(s) to said sentence(s) in a mapping table created by domain experts and,
    (c) looking up corresponding sentence(s) to said sentential proposition(s) in said mapping table and,
    (d) retrieving document templates from a document collection that contain one or more of said sentence(s) into separate partial solution sets and,
    (e) performing a Boolean "AND" operations on said partial solution sets,
Whereby a solution set of document templates is returned.

10. The method according to claim 9 where the input sentence(s) are acquired through speech recognition.

11. The method according to claim 9 where the input sentence(s) are acquired through a word processor.

12. The method according to claim 9 wherein a count of unique template documents in the solution set is displayed.

13. The method according claim 9 wherein sentence(s) from a template document in the solution set are displayed as a list which are transferred to a document under construction in response to user selection.

14. The method according to claim 9 wherein a user restricts the documents from the solution set to a subset consisting of either personal templates, departmental templates, or company wide templates, or any combination thereof.

15. The method according to claim 9 wherein a user restricts the sentences to specific sections within the template document collection.

* * * * *